United States Patent [19]

Oh et al.

[11] Patent Number: 4,704,272

[45] Date of Patent: Nov. 3, 1987

[54] SHAMPOO COMPOSITIONS

[75] Inventors: Young S. Oh, Fairfield; Richard M. Dahlgren, Cincinnati; Glen D. Russell, Middletown, all of Ohio

[73] Assignee: The Procter & Gamble Company, Cincinnati, Ohio

[21] Appl. No.: 753,307

[22] Filed: Jul. 10, 1985

[51] Int. Cl.$^4$ .............................................. A61K 7/06
[52] U.S. Cl. ....................................... 424/70; 514/938
[58] Field of Search ........................... 424/70; 252/547

[56] References Cited

U.S. PATENT DOCUMENTS

| | | | |
|---|---|---|---|
| 2,826,551 | 3/1958 | Geen | 252/89 |
| 3,849,348 | 11/1974 | Hewitt | 252/547 |
| 3,950,510 | 4/1976 | Adams | 424/70 |
| 3,957,970 | 5/1976 | Korkis | 424/70 |
| 3,964,500 | 6/1976 | Drakoff | 132/7 |
| 4,278,657 | 7/1981 | Tezuka et al. | 424/63 |
| 4,364,837 | 12/1982 | Pader | 252/173 |
| 4,452,732 | 6/1984 | Bolich, Jr. | 252/547 |
| 4,465,619 | 8/1984 | Boskamp | 252/540 |
| 4,470,982 | 9/1984 | Winkler | 424/245 |
| 4,597,962 | 7/1986 | Grollier et al. | 424/47 |

FOREIGN PATENT DOCUMENTS 849433  9/1960  United Kingdom ................. 424/70

OTHER PUBLICATIONS

Bennett, H., Editor, 1974 *Chemical Formulary* vol. XVIII, p. 167.

Hennock, M. et al., "Effect of Xanthan Gum and Stability of Oil-Water Emulsions" Journal of Food Science vol. 49 (1984) pp. 1271–1279.

*Primary Examiner*—Dale R. Ore
*Attorney, Agent, or Firm*—Richard C. Witte; John V. Gorman; Douglas C. Mohl

[57] ABSTRACT

Shampoos are disclosed which comprise a synthetic anionic surfactant, a dispersed, insoluble, non-volatile silicone, a tri long chain alkyl quaternary ammonium salt or a tri long chain amine, a suspending agent and water.

17 Claims, No Drawings

SHAMPOO COMPOSITIONS

TECHNICAL FIELD

The present invention is related to conditioning shampoos which have improved hair conditioning properties due to the inclusion of a particular type of quaternary ammonium salt or amine and an insoluble, non-volatile silicone.

BACKGROUND OF THE INVENTION

Human hair becomes soiled due to its contact with the surrounding atmosphere and, to a greater extent, from sebum secreted by the head. The build-up of the sebum causes the hair to have a dirty feel and an unattractive appearance. The soiling of the hair necessitates it being shampooed with frequent regularity.

Shampooing the hair cleans by removing excess soil and sebum. However, the shampooing process has disadvantages in that the hair is left in a wet, tangled and generally unmanageable state. A variety of approaches have been developed to alleviate the after-shampoo problems. These range from the inclusion of hair conditioning aids in shampoos to post-shampoo application of hair conditioners, i.e., hair rinses. Hair rinses typically work by depositing a polymeric film or other material onto the hair. However, such solutions to a very prevalent problem have not been fully satisfactory. For one thing, hair rinses are generally liquid in nature and must be applied in a separate step following the shampooing, left on the hair for a length of time, and rinsed with fresh water. This, of course, is time consuming and is not convenient.

While shampoos have been disclosed which contain conditioning aids, they have not been totally satisfactory for a variety of reasons. One problem relates to compatibility problems between good cleaning anionic surfactants and the fatty cationic agents which are good conditioning agents. This has caused other surfactants such as nonionics, amphoterics and zwitterionics to be examined by workers in the field. Many of these efforts are reflected in patents issued in the conditioning shampoo area. See for example U.S. Pat. No. 3,849,348, Nov. 19, 1974 to Hewitt; U.S. Pat. No. 3,990,991, Nov. 9, 1961 to Gerstein; and U.S. Pat. No. 3,822,312, July 2, 1974 to Sato.

The use of these other surfactants solved many of the compatibility problems but still did not provide complete answers in all areas. For instance cationic conditioners may not deliver the desired level of softness desired by users. Materials which can provide increased softness are silicones, both those which are soluble as well as insoluble in the shampoo matrix.

Silicones in shampoo compositions have been disclosed in a number of different publications. Such publications include U.S. Pat. No. 2,826,551, Mar. 11, 1958 to Geen; U.S. Pat. No. 3,964,500, June 22, 1976 to Drakoff; U.S. Pat. No. 4,364,837, Dec. 21, 1982 to Pader; British Pat. No. 849,433, Sept. 28, 1960 to Woolston; U.S. Pat. No. 4,341,799, July 27, 1982 to Good, and U.S. Pat. No. 4,465,619, Aug. 14, 1984 to Boskamp. While these patents disclose silicone containing compositions, they also do not provide answers to all of the problems encountered in making a totally satisfactory product. One unsolved problem is that of providing satisfactory static control as well as other hair conditioning properties such as softness and wet and dry combing. Although the patents listed above disclose the inclusion of cationic materials with silicones, they do not disclose or suggest using materials which allow for good hair conditioning and stable products.

It is an object of the present invention to provide a superior conditioning shampoo containing a silicone material and a particular quaternary material or amine which is compatible with other materials in the shampoo matrix.

It is a further object of the present invention to provide such shampoo compositions which possess good stability.

It is a further object of the present invention to provide an improved method of shampooing and conditioning hair.

These and other objects will become readily apparent from the detailed description which follows.

Unless otherwise indicated, all percentages and ratios herein are by weight.

SUMMARY OF THE INVENTION

The present invention relates to shampoo compositions comprising from about 5% to about 50% of a synthetic anionic surfactant, about 0.1% to about 10.0% of an insoluble, non-volatile, dispersed silicone, about 0.1% to about 4% of a tri long chain alkyl quaternary ammonium salt or a tri long chain amine, about 0.4% to about 3% of a suspending agent and water. These as well as optional components are described in detail below.

DETAILED DESCRIPTION

The essential and optional components of the present invention are given in the following paragraphs.

Surfactant

An essential component of the present compositions is a synthetic anionic surfactant. The surfactant is present at a level of from about 5% to about 50%, preferably from about 10% to about 30%.

Synthetic anionic detergents useful herein include alkyl and alkyl ether sulfates. These materials have the respective formulae $ROSO_3M$ and $RO(C_2H_4O)_xSO_3M$ wherein R is alkyl or alkenyl of about 10 to about 20 carbon atoms, x is 1 to 10, and M is a water-soluble cation such as ammonium, sodium, potassium and triethanolamine. The alkyl ether sulfates useful in the present invention are condensation products of ethylene oxide and monohydric alcohols having about 10 to about 20 carbon atoms. Preferably, R has 14 to 18 carbon atoms in both the alkyl and alkyl ether sulfates. The alcohols can be derived from fats, e.g., coconut oil or tallow, or can be synthetic. Lauryl alcohol and straight chain alcohols derived from coconut oil are preferred herein. Such alcohols are reacted with 1 to 10, and especially 3, molar proportions of ethylene oxide and the resulting mixture of molecular species, having, for example, an average of 3 moles of ethylene oxide per mole of alcohol, is sulfated and neutralized.

Specific examples of alkyl ether sulfates of the present invention are sodium coconut alkyl trioxyethylene sulfate; lithium tallow alkyl trioxyethylene sulfate; and sodium tallow alkyl hexaoxyethylene sulfate. Highly preferred alkyl ether sulphates are those comprising a mixture of individual compounds, said mixture having an average alkyl chain length of from about 12 to 16 carbon atoms and an average degree of ethoxylation of from about 1 to 4 moles of ethylene oxide. Such a mixture also comprises from about 0 to 20% by weight $C_{12-13}$ compounds; from 60 to 100% by weight of $C_{14-15-16}$ compounds, from about 0 to 20% by weight of $C_{17-18-19}$ compounds; from about 3 to 30% by weight of compounds having a degree of ethoxylation of 0; from about 45 to 90% by weight of compounds having a degree of ethoxylation of from 1 to 4; from about 10 to 25% by weight of compounds having a degree of ethoxylation of from 4 to 8; and from about 0.1 to 15% by weight of compounds having a degree of ethoxylation greater than 8.

Additional examples of anionic synthetic detergents which come within the terms of the present invention are the reaction product of fatty acids esterified with isethionic acid and neutralized with sodium hydroxide where, for example, the fatty acids are derived from coconut oil; sodium or potassium salts of fatty acid amides of methyl tauride in which the fatty acids, for example, are derived from coconut oil. Other anionic synthetic detergents of this variety are set forth in U.S. Pat. Nos. 2,486,921; 2,486,922; and 2,396,278.

Still other anionic synthetic detergents include the class designated as succinamates. This class includes such surface active agents as disodium N-octadecylsulfosuccinamate; tetrasodium N-(1,2-dicarboxyethyl)-N-octadecylsulfo-succinamate; diamyl ester of sodium sulfosuccinic acid: dihexyl ester of sodium sulfosuccinic acid; dioctyl esters of sodium sulfosuccinic acid.

Other suitable anionic detergents utilizable herein are olefin sulfonates having about 12 to about 24 carbon atoms. The term "olefin sulfonates" is used herein to mean compounds which can be produced by the sulfonation of α-olefins by means of uncomplexed sulfur trioxide, followed by neutralization of the acid reaction mixture in conditions such that any sultones which have been formed in the reaction are hydrolyzed to give the corresponding hydroxy-alkanesulfonates. The sulfur trioxide can be liquid or gaseous, and is usually, but not necessarily, diluted by inert diluents, for example by liquid $SO_2$, chlorinated hydrocarbons, etc., when used in the liquid form, or by air, nitrogen, gaseous $SO_2$, etc., when used in the gaseous form.

The α-olefins from which the olefin sulfonates are derived are mono-olefins having 12 to 24 carbon atoms, preferably 14 to 16 carbon atoms. Preferably, they are straight chain olefins. Examples of suitable 1-olefins include 1-dodecene; 1-tetradecene; 1-hexadecene; 1-octadecene; 1-cicosene and 1-tetraeosene.

In addition to the true alkene sulfonates and a proportion of hydroxy-alkanesulfonates, the olefin sulfonates can contain minor amounts of other materials, such as alkene disulfonates depending upon the reaction conditions, proportion of reactants, the nature of the starting olefins and impurities in the olefin stock and side reactions during the sulfonation process.

A specific α-olefin sulfonate mixture of the above type is described more fully in the U.S. Pat. No. 3,332,880 of Phillip F. Pflaumer and Adrian Kessler, issued July 25, 1967, titled "Detergent Composition", the disclosure of which is incorporated herein by reference.

Another class of anionic organic detergents are the β-alkyloxy alkane sulfonates. These compounds have the following formula:

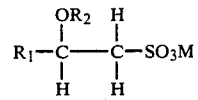

where $R_1$ is a straight chain alkyl group having from 6 to 20 carbon atoms, $R_2$ is a lower alkyl group having from 1 (preferred) to 3 carbon atoms, and M is a water-soluble cation as hereinbefore described.

Specific examples of β-alkyloxy-alkane-1-sulfonates, or alternatively 2-alkyloxy-alkane-1-sulfonates, having low hardness (calcium ion) sensitivity useful herein to provide superior cleaning levels under household washing conditions include: potassium-β-methoxydecanesulfonate, sodium 2-methoxytridecanesulfonate, potassium 2-ethoxytetradecylsulfonate, sodium 2-isopropoxyhexadecylsulfonate, lithium 2-t-butoxytetradecylsulfonate, sodium-methoxyoctadecylsulfonate, and ammonium-n-propoxydodecylsulfonate.

Another suitable class of anionic surfactants are the water-soluble salts of the organic, sulfuric acid reaction products of the general formula:

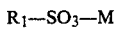

wherein $R_1$ is chosen from the group consisting of a straight or branched chain, saturated aliphatic hydrocarbon radial having from 8 to 24, preferably 12 to 18, carbon atoms; and M is a cation. Important examples are the salts of an organic sulfuric acid reaction product of a hydrocarbon of the methane series, including iso-, neo-, ineso-, and n-paraffins, having 8 to 24 carbon atoms, preferably 12 to 18 carbon atoms and a sulfonating agent e.g., $SO_3$, $H_2SO_4$, oleum, obtained according to known sulfonation methods, including bleaching and hydrolysis. Preferred are alkali metal and ammonium sulfonated $C_{12-18}$-n-paraffins.

Many additional nonsoap synthetic anionic surfactants are described in McCUTCHEON'S, DETERGENTS AND EMULSIFIERS, 1984 ANNUAL, published by Allured Publishing Corporation, which is incorporated herein by reference. Also U.S. Pat. No. 3,929,678, Dec. 30, 1975 to Laughlin et al. discloses many other anionic as well as other surfactant types and is incorporated herein by reference.

The above-mentioned surfactants can be used alone or in combination in the shampoo compositions of the present invention. The alkyl sulfates, the ethoxylated alkyl sulfates and mixtures thereof are preferred for use herein.

Non-Volatile Silicone Fluid

The non-volatile silicone fluid may be either a polyalkyl siloxane, a polyaryl siloxane, a polyalkylaryl siloxane or a polyether siloxane copolymer and is present at a level of from about 0.1% to about 10.00% preferably from about 0.5% to about 5.0%. Mixtures of these fluids may also be used and are preferred in certain executions. The dispersed silicone particles should also be insoluble in the shampoo matrix. This is the meaning of "insoluble" as used hereinbefore and hereinafter.

The essentially non-volatile polyalkyl siloxanes that may be used include, for example, polydimethyl siloxanes with viscosities ranging from about 5 to 600,000 centistokes at 25° C. These siloxanes are available, for example, from the General Electric Company as the Viscasil series and from Dow Corning as the Dow Corning 200 series. The viscosity can be measured by means of a glass capillary viscometer as set forth in Dow Corning Corporate Test Method CTM0004, July 20, 1970. Preferably the viscosity ranges from about 350 centistokes to about 100,000 centistokes.

The essentially non-volatile polyalkylaryl siloxanes that may be used include, for example, polymethylphenylsiloxanes having viscosities of about 15 to 65 centistokes at 25° C. These siloxanes are available, for example, from the General Electric Company as SF 1075 methyl phenyl fluid or from Dow Corning as 556 Cosmetic Grade Fluid.

The essentially non-volatile polyether siloxane copolymer that may be used is, for example, a polypropylene oxide modified dimethylpolysiloxane (e.g., Dow Corning DC-1248) although ethylene oxide or mixtures of ethylene oxide and propylene oxide may also be used.

References disclosing suitable silicones include the previously mentioned U.S. Pat. No. 2,826,551 to Geen, U.S. Pat. No. 3,964,500, June 22, 1976 to Drakoff; U.S. Pat. No. 4,364,837 to Pader and British Pat. No. 849,433 to Woolston. All of these patents are incorporated herein by reference. Also incorporated herein by reference is *Silicon Compounds* distributed by Petrarch Systems, Inc., 1984. This reference provides a very good listing of suitable silicone materials. Materials found especially useful are silicone gums described by Petrarch and others. Two other references include U.S. Pat. No. 4,152,416, May 1, 1979 to Spitzer et al. and Noll, Walter, *Chemistry and Technology of Silicones*, New York: Academic Press 1968. Both of these references are incorporated herein by reference. The silicone gum materials generally have a molecular weight of from about 200,000 to about 700,000.

Hair Conditioning Agent

A compound useful in the present invention is a tri long chain alkyl mono short chain alkyl quaternary ammonium salt or a tri long chain amine. By "long" is meant having from about 8 to about 22 carbon atoms while "short" includes alkyls having from about 1 to about 4 carbon atoms. A preferred material is tricetyl methyl ammonium chloride. Other halides such as bromide and iodide or organic groups such as methyl sulfate may be used to form the salt. Other specific compounds include tri $C_{8-10}$ methyl ammonium chloride, tri(isodecyl)amine and tri $C_{13}$ amine. The quaternary compound or amine is used at a level of from about 0.1% to about 4%, preferably from about 0.25% to about 2%.

Suspending Agent

Another essential component of the present compositions is a suspending agent. Two preferred materials are xanthan gum and long chain acyl derivatives as well as other long chain materials.

Xanthan gum is an agent which can be used in the present compositions to suspend the silicone fluid. This biosynthetic gum material is commercially available and is a heteropolysaccharide with a molecular weight of greater than 1 million. It contains D-glucose, D-mannose and D-glucuronate in the molar ratio of 2.8:2.0:2.0. The polysaccharide is partially acetylated with 4.7% acetyl. This information and other is found in Whistler, Roy L. Editor *Industrial Gums—Polysaccharides and Their Derivatives* New York: Academic Press, 1973. Kelco, a Division of Merck & Co., Inc. offers xanthan gum as Keltrol ®. The gum is present at a level of from about 0.4% to about 3%, preferably from about 0.6% to about 1.2% in the compositions of the present invention.

Another suspending agent useful in the present compositions is any of several long chain acyl derivatives materials or mixtures of such materials. Included are ethylene glycol esters of fatty acids having from about 16 to about 22 carbon atoms. Preferred are the ethylene glycol stearates, both mono and distearate, but particularly the distearate containing less than about 7% of the mono stearate. Other suspending agents found useful are alkanol amides of fatty acids, having from about 16 to about 22 carbon atoms, preferably about 16 to 18 carbon atoms. Preferred alkanol amides are stearic monoethanolamide, stearic diethanolamide, stearic monoisopropanolamide and stearic monoethanolamide stearate.

Still other suitable non-acyl derivative suspending agents are alkyl($C_{16-22}$)dimethyl amine oxides such as stearyl dimethyl amine oxide.

The suspending agent or mixtures of agent is present at a level of from about 0.4% to about 5%, preferably from about 0.5% to about 2.5%. The suspending agent serves to assist in suspending the silicone material and may also give pearlescence to the product.

Water

Water is the last essential component of the present invention and forms the remainder of the composition. It is generally present at a level of from about 20% to about 95%, preferably from about 60% to about 85%.

Optional Components

The shampoos herein can contain a variety of nonessential optional components suitable for rendering such compositions more acceptable. Such conventional optional ingredients are well known to those skilled in the art, e.g., preservatives such as benzyl alcohol, methyl paraben, propyl paraben and imidazolidinyl urea; other cationic surfactants such as lauryl trimethyl ammonium chloride, cetyl trimethyl ammonium chloride, stearyldimethyl benzyl ammonium chloride, and di(partially hydrogenated tallow) dimethylammonium chloride; thickeners and viscosity modifiers such as a diethanolamide of a long chain fatty acid (e.g., Cocamide MEA), amine oxides, block polymers of ethylene oxide and propylene oxide such as Pluronic F88 offered by BASF Wyandotte, fatty alcohols such as cetearyl alcohol, sodium chloride, sodium sulfate, polyvinyl alcohol, and ethyl alcohol; pH adjusting agents such as mono sodium phosphate and disodium phosphate, citric acid, succinic acid, phosphoric acid, sodium hydroxide, sodium carbonate, etc.; perfumes; dyes; and, sequestering agents such as disodium ethylenediamine tetraacetate. Such agents generally are used individually at a level of from about 0.01% to about 10%, preferably from about 0.5% to about 5.0% by weight of the composition.

Another optional ingredient and one preferred for use in certain of the compositions of this invention, is a volatile silicone or a water insoluble hydrocarbon. These agents are disclosed in U.S. Pat. No. 4,472,375, Sept. 18, 1984 to R. E. Bolich, Jr. incorporated herein by reference. These agents help disperse the higher molecular weight, non-volatile silicones in the product when such silicones are used. These agents are used at levels from about 0.1% to about 5%.

The pH of the present compositions is not critical and may be in the range of from 4 to about 10.

METHOD OF MANUFACTURE

The present compositions can be made by preparing both a main mix and a premix. Referring to the compositions of the Examples, into the main mix tank are put the ammonium lauryl sulfate, a part of the ammonium laureth sulfate and the ammonium xylene sulfonate. This mixture is heated to 120±10° F. with xanthan gum added next through a high shear pump. The total mixture is then heated to 155±5° F. Finally the glycol distearate, amide, part of the cetearyl alcohol and lauryl trimethyl ammonium chloride are added followed by the tricetyl methyl ammonium chloride, color, perfume, perservative and part of the water.

The premix is prepared by adding the remainder of the ammonium laureth sulfate to the premix tank and heating to 155±5° F. The remainder of the cetearyl alcohol is then added and allowed to melt. Finally the dimethicone is added and mixed until an emulsion is formed.

The premix is mixed with the main mix through a static mixers, a high shear mixer and finally through a heat exchanger. The total product is cooled to 80° F. and collected.

INDUSTRIAL APPLICABILITY

The present compositions are used in a conventional manner for cleaning hair. From about 0.1 g to about 10 g of a composition is applied to hair that has been wetted, generally with water, worked through the hair and then rinsed out.

The following Examples further describe and demonstrate the preferred embodiments within the scope of the present invention. The Examples are given solely for the purpose of illustration and are not to be construed as limitations of the present invention as many variations thereof are possible without departing from its spirit and scope.

EXAMPLES I-VI

The following compositions representative of the present invention are prepared.

| Component | I | II | III | IV | V | VI |
| --- | --- | --- | --- | --- | --- | --- |
| Ammonium Lauryl Sulfate | 12.00 | 12.00 | 12.00 | 15.00 | 8.00 | 8.00 |
| Ammonium Laureth (3) Sulfate | 4.00 | 4.00 | 4.00 | 4.00 | 8.00 | 8.0 |
| Ammonium Xylene Sulfonate | 2.20 | 2.20 | 3.00 | — | — | |
| Cetearyl Alcohol | 1.00 | 1.00 | 0.10 | 0.50 | 1.00 | 1.00 |
| Glycol Distearate | 0.75 | 2.50 | 0.75 | 0.75 | 0.75 | 0.75 |
| Cocamide MEA | 1.00 | 1.50 | 1.00 | 1.00 | 1.00 | 1.00 |
| Xanthan Gum | 0.75 | — | 0.75 | 0.75 | 0.75 | 0.75 |
| Dimethicone Fluid Viscosity 350 centistokes | 1.80 | 1.80 | 1.80 | 1.80 | 1.80 | 1.80 |
| Silicone Gum | 1.00 | 1.00 | 1.00 | 1.00 | 1.00 | 1.00 |
| Lauryl Trimethyl | — | — | 0.75 | 0.75 | — | — |
| Tricetyl Methyl Ammonium Chloride | 1.00 | 0.50 | 0.50 | 0.50 | — | — |
| Tri C$_{8-10}$ Methyl Ammonium Chloride | — | — | — | — | 2.00 | — |
| Tri C$_{13}$ Amine | — | — | — | — | — | 2.00 |
| Color, Perfume, Preservative, pH control and Water q.s. 100%→ | | | | | | |

These compositions all deliver good hair conditioning while also providing good cleaning.

What is claimed is:

1. A shampoo composition comprising:
   (a) from about 5% to about 50% of synthetic anionic surfactant or mixtures thereof;
   (b) from about 0.1% to about 10% of a dispersed, insoluble, non-volatile silicone or mixtures thereof;
   (c) from about 0.1% to about 4% of a hair conditioning agent selected from the group consisting of tri long chain alkyl mono short chain alkyl quaternary ammonium salts, tri long chain alkyl amines and mixtures thereof;
   (d) from about 0.4% to about 5% of a suspending agent
   (e) the remainder water.

2. A shampoo composition according to claim 1 wherein the surfactant is selected from the group consisting of alkyl sulfates, ethoxylated alkyl sulfates, alpha olefin sulfonates alkyl sulfonates and mixtures thereof.

3. A shampoo composition according to claim 2 wherein the non-volatile silicone has viscosity of from about 5 to about 600,000 centistokes at 25° C.

4. A shampoo composition according to claim 2 wherein the hair conditioning agent is a quaternary ammonium salt.

5. A shampoo composition according to claim 3 wherein the surfactant is selected from the group consisting of alkyl sulfates, ethoxylated alkyl sulfates and mixtures thereof.

6. A shampoo composition according to claim 4 wherein the non-volatile silicone is a polydimethylsiloxane.

7. A shampoo composition according to claim 5 wherein an amide is also present in the compositions.

8. A shampoo composition according to claim 6 wherein the surfactant is an alkyl sulfate.

9. A shampoo composition according to claim 8 wherein the surfactant is ammonium alkyl sulfate.

10. A shampoo composition according to claim 1 wherein the non-volatile silicone composition is a mixture of non-volatile silicones.

11. A shampoo composition according to claim 10 wherein one of the non-volatile silicones is a silicone gum.

12. A shampoo composition according to claim 11 wherein the quaternary ammonium compound is tricetyl methyl ammonium chloride.

13. A method of shampooing hair comprising applying from about 0.1 g to about 10 g of a composition according to claim 1 to hair that has been wet with water and then rinse out.

14. A method according to claim 13 wherein the composition is in accordance with claim 4.

15. A method according to claim 13 wherein the composition is in accordance with claim 10.

16. A method according to claim 13 wherein the composition is in accordance with claim 11.

17. A method according to claim 13 wherein the composition is in accordance with claim 12.

* * * * *